United States Patent [19]
Yoshioka et al.

[11] Patent Number: 4,981,986
[45] Date of Patent: Jan. 1, 1991

[54] ORGANOSILICON COMPOUND

[75] Inventors: Hiroshi Yoshioka; Masaaki Yamaya, both of Annaka; Kazuharu Sato, Gunma; Akinari Itagaki, Annaka, all of Japan

[73] Assignee: Shin-Etsu Chemical Co., Japan

[21] Appl. No.: 178,318

[22] Filed: Apr. 6, 1988

[30] Foreign Application Priority Data

Apr. 6, 1987 [JP] Japan .................................. 62-84218

[51] Int. Cl.$^5$ .............................. C07F 7/10; C07F 7/04
[52] U.S. Cl. ..................................... 556/410; 556/440
[58] Field of Search .................. 556/410, 440, 40, 436

[56] References Cited

U.S. PATENT DOCUMENTS 3,624,121 11/1971 Terry ................................... 556/436
4,808,649 2/1989 Gay et al. ............................ 556/440

Primary Examiner—John Doll
Assistant Examiner—Stuart L. Hendrickson

[57] ABSTRACT

Disclosed herein is a new organosilicon compound having a β-diketone or β-ketoester structures and a hydrolyzable group. The new organosilicon compound can be effectively used for the production of an immobilized catalyst, an adsorbent for metal recovery, a curing catalyst for organosiloxane and epoxy resins, and an adhesion promoter.

4 Claims, No Drawings

ORGANOSILICON COMPOUND

BACKGROUND OF THE INVENTION

1. Field of the Invention:

The present invention relates to a new organosilicon compound having a β-diketone or β-ketoester structure and a hydrolyzable group. More particularly, it relates to an organosilicon compound represented by formula (1) below.

where R denotes a monovalent organic group containing
one or more β-diketone or β-ketoester structures having 4 to 20 carbon atoms; X denotes a hydrolyzable group selected from a halogen atoms an alkoxy group having 1 to 6 carbon atoms, an acyloxy group having 1 to 6 carbon atoms, and an amino group; m denotes 1, 2, or 3; n denotes 0, 1, or 2; and $1 \leq m + n \leq 3$.)

The present invention also relates to an organosilicon compound produced by the intramolecular and/or intermolecular condensation of the organosilicon compound represented by formula (1).

2. Description of the Prior Art:

Heretofore, organosilicon compounds have been used as an immobilized catalyst, an adsorbent for the recovery of metals from solutions, and a curing catalyst for organopolysiloxanes and epoxy resins. However, there have not been any organosilicon compounds which fully exhibit their performance in these application areas.

SUMMARY OF THE INVENTION

The present invention was completed under these circumstances. Accordingly, it is an object of the present invention to provide a new organosilicon compound which can be effectively used for the production of an immobilized catalyst, an adsorbent for metal recovery, a curing catalyst for organopolysiloxanes and epoxy resins, and an adhesion promoter.

The present inventors carried out a series of researches to achieve the above-mentioned object. As a result, it was found that it is possible to obtain a new organosilicon compound represented by formula (1) below

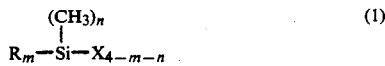

where R denotes a monovalent organic group containing one or more β-diketone or β-ketoester structures having 4 to 20 carbon atoms; X denotes a hydrolyzable group selected from a halogen atom, an alkoxy group having 1 to 6 carbon atoms, an acyloxy group having 1 to 6 carbon atoms, and an amino group; m denotes 1, 2, or 3; n denotes 0, 1, or 2; and $1 \leq m + n \leq 3$.by the hydrosilylation reaction which involves the reaction of a silicon compound having a ≡SiH group with a compound having both a β-diketone or β-ketoester structure and an unsaturated group in one molecule. It was also found that it is possible to obtain another new organosilicon compound by the intramolecular and/or intermolecular condensation of the organosilicon compound of formula (1).

More specifically, another new organosilicon compound can be produced through an intermolecular or intramolecular condensation between an OH group and a hydrolyzable group, the OH group being the one formed through the keto/enol tautomerism of a β-diketone or β-ketoester contained in the organosilicon compound represented by formula (1), and the hydrolyzable group being the one contained in the organosilicon compound represented by formula (1).

The new organosilicon compound having at least one β-diketone or β-ketoester structure and at least one hydrolyzable group in the molecule readily forms a complex structure with a metal compound through the coordinate bond of the β-diketone or β-ketoester structure, and also combines with an inorganic compound or active hydrogen compound through the reaction of the hydrolyzable group. In addition, the organosilicon compound can be introduced into the skeleton of polyorganosiloxane by hydrolysis and condensation. Because of these two characteristic features, the organosilicon compound is expected to find uses in a wide variety of industrial fields.

When used for surface treatment, the organosilicon compound provides particles such as silica particles the ability to combine with a metal compound. The surface of the particles treated with the organosilicon compound can be used as a carrier for an immobilized catalyst of active metal compound surface, and also can be used as an adsorbent to recover dissolved metal compounds from a solution. Moreover, the organosilicon compound increases the activity of curing catalysts for organopolysiloxanes and epoxy resins because the compound readily combines with a metal compound. Another use of the organosilicon compound is to improve the bond strength between a glass object and an epoxy resin. This is accomplished by treating the glass object with the organosilicon compound, permitting the coating of the organosilicon compound to react with a metal compound, and pouring an epoxy resin onto (or into) the glass object. The bond strength thus achieved is maintained even under humid conditions.

The above and other objects, features and advantages of the present invention will be more apparent from the following description.

DETAILED DESCRIPTION OF THE INVENTION

The present invention provides a new organosilicon compound represented by formula (1) above and also another new organosilicon compound which is obtained by the intramolecular and/or intermolecular condensation of an organosilicon compound represented by formula (1) above.

In formula (1), R denotes a monovalent organic group containing one or more of β-diketone of β-ketoester structures having 4 to 20 carbon atoms. Examples of R include the following.

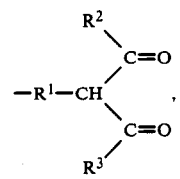

-continued

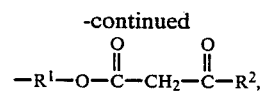

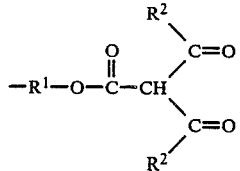

and

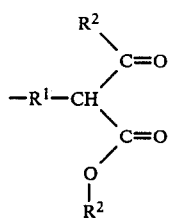

wherein $R^1$ represents an aromatic or aliphatic divalent hydrocarbon group having 1 to 9 carbon atoms, and $R^2$ represents a monovalent hydrocarbon group having 1 to 6 carbon atoms. $R^1$ includes —$CH_2$—, —$CH_2CH_2CH_2$—,

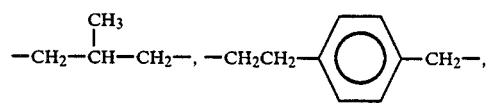

$R^2$ includes $CH_3$—, $CH_3CH_2$—, $CH_3CH_2CH_2$—, $CH_3CH_2CH_2CH_2$—

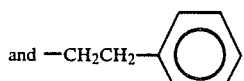

The preferred Rs are shown below.

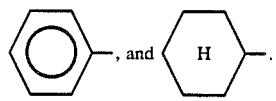

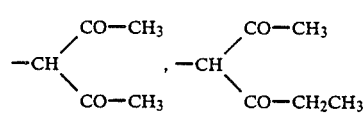

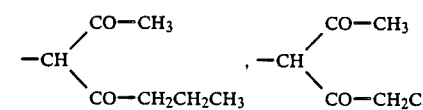

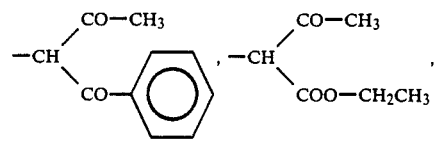

-continued

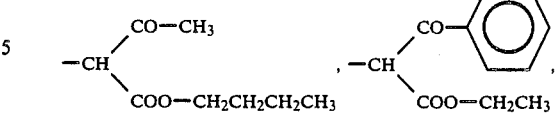

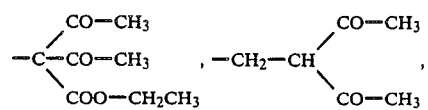

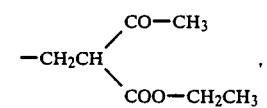

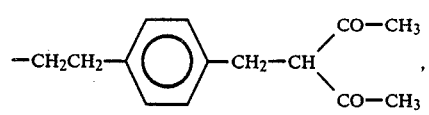

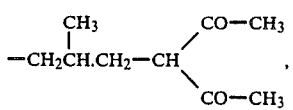

—$CH_2CH_2CH_2$—OOC—$CH_2$—CO—$CH_2CH_2CH_2CH_3$,
—$CH_2CH_2CH_2$—OOC—$CH_2$—CO—$CH_3$,

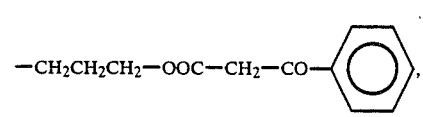

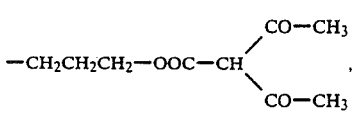

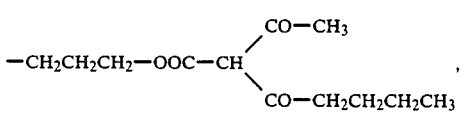

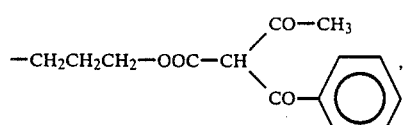

and

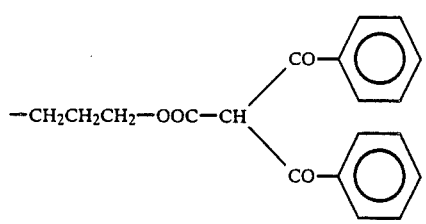

In formula (1), X denotes a hydrolyzable group. Examples of X include a halogen atom such as —Cl, —Br, and —I; an alkoxy group having 1 to 6 carbon atoms such as —$OCH_3$, —$OCH_2CH_3$, —$OCH_2CH_2CH_3$, —$OCH_2CH_2CH_2CH_3$, —OCH(CH₃)—CH₃, —O—C(CH₃)=CH₂, —O—C(CH₃)=CH—CH₃, and

—O—C₆H₅;

an acyloxy group having 1 to 6 carbon atoms such as —OOC—CH₃ and —OOC—CH₂CH₂CH₃; and an amino group represented by formula $$-N\begin{matrix}H\\R'\end{matrix}$$

wherein R' denotes a hydrogen atom or an alkyl group having 1 to 4 carbon atoms, such as —NH₂, —NH—CH₃, and —NH—CH₂CH₂CH₂CH₃.

In formula (1), m denotes the number of the monovalent organic groups having the β-diketone or β-ketoester structure. It denotes 1, 2, or 3.

In formula (1), n denotes the number of methyl groups. It denotes 0, 1, or 2.

The following are the examples of the organosilicon compound represented by formula (1) below $$R_m-\underset{\underset{X_{4-m-n}}{|}}{\overset{\overset{(CH_3)_n}{|}}{Si}} \quad (1)$$

where R, X, m and n are defined as above, The examples are:

(CH₃O)₃Si—CH₂CH₂CH₂—O—CO—CH₂—CO—CH₃, (CH₃CH₂O)₃Si—CH₂CH₂CH₂—O—CO—CH₂—CO—CH₃, (CH₃—CO—O)₃Si—CH₂CH₂CH₂—O—CO—CH₂—CO—CH₃, (CH₂=C(CH₃)—O)₃Si—CH₂CH₂CH₂—O—CO—CH₂—CO—CH₃, (CH₃O)₂Si(CH₃)—CH₂CH₂CH₂—O—CO—CH₂—CO—CH₃,

CH₃O—Si(CH₃)₂—CH₂CH₂CH₂—O—CO—CH₂—CO—CH₃, (CH₃O)₃Si—CH₂CH₂CH₂—O—CO—CH(CO—CH₃)—CO—CH₃, (CH₃O)₃Si—CH₂CH₂CH₂—O—CO—CH₂—CO—CH₂CH₂CH₃,

-continued (CH₃O)₃Si—CH₂CH₂CH₂—O—CO—CH₂—CO—C₆H₅, (CH₃O)₃Si—CH(CO—CH₃)(CO—CH₃), (CH₃O)₃Si—CH(CO—CH₃)(CO—CH₂CH₂CH₃), (CH₃O)₃Si—CH(CO—CH₃)(CO—O—CH₂CH₃), (CH₃O)₃Si—CH(CO—C₆H₅)(CO—O—CH₂CH₃), (CH₃O)₃Si—CH₂—CH(CO—CH₃)(CO—CH₃), (CH₃O)₃Si—CH₂—CH(CO—CH₃)(COO—CH₂CH₃), (CH₃O)₃Si—CH₂CH₂CH₂—CH(CO—CH₃)(CO—CH₃), (CH₃O)₃Si—CH₂CH₂CH₂—CH(CO—CH₃)(COO—CH₂CH₃), (CH₃O)₃Si—CH₂CH₂—C₆H₄—CH₂—CH(CO—CH₃)(CO—CH₃), (CH₃O)₃Si—CH₂CH₂—C₆H₄—CH₂—CH(CO—CH₃)(COO—CH₂CH₃), (CH₃O)₃Si—CH₂—CH(CH₃)—CH₂—CH(CO—CH₃)(CO—CH₃), and -continued

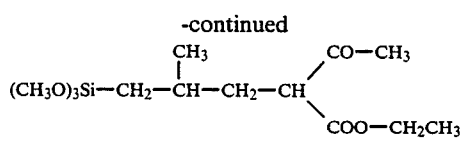

The organosilicon compound represented by formula (1) has at least one β-diketone or β-ketoester structure in the molecule, which readily changes into an OH group through the keto/enol tautomerism. The OH group reacts with the hydrolyzable group connected to the silicon atom in the organosilicon compound of formula (1). Therefore, the intermolecular or intramolecular condensation easily occurs. The thus formed condensation product is also a new organosilicon compound of the present invention. The following are the examples of such a compound.

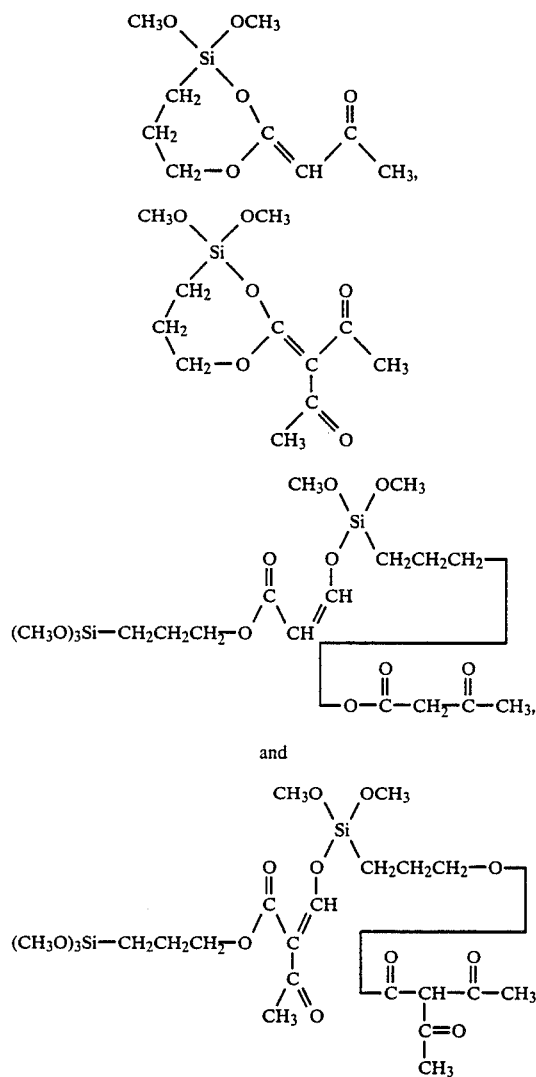

and

The new organosilicon compound can be produced by either of the following two processes.

According to the first process, a silicon compound having both a hydrolyzable group and a ≡Si—H group is reacted with a compound having both β-diketone or β-ketoester structure and an unsaturated group such as alkenyl group (e.g. vinyl group or allyl group) in one molecule, in the presence of a catalyst such as a transition metal (e.g. Pt, Rh or Pd) compound. This is the hydrosilylation reaction represented by equation (i) below.

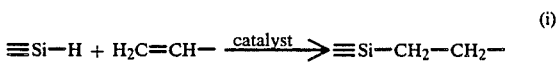
(i)

The reaction may be carried out at 20° to 100° C. for 1 to 10 hours.

For example, a new organosilicon compound represented by the formula below can be obtained by reacting allyldiacetoacetate with trimethoxysilane in the presence of chloroplatinic acid, as mentioned later in the Examples.

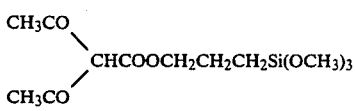

According to the second process, an alkali metal compound is reacted with a halogen compound or alkoxy compound containing a silicon which connects to at least one hydrolyzable group. This reaction is represented by equation (ii) below.

$$R^1—M+X^1—R^2—Si\equiv \rightarrow R^1—R^2—Si\equiv ...$$ (ii)

where M denotes an alkali metal or $MgX^2$ ($X^2$ denotes halogen atom); $R^1$ denotes a monovalent organic group containing β-diketone or β-ketoester structure; and $R^2$ denotes a divalent organic group such as a —CH₂— group, —CH₂CH₂CH₂—group,

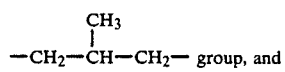
group, and

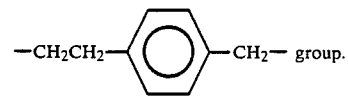

$X^1$ denotes a halogen atom, —OCH₃ group, —OCH₂CH₃ group, —OCH₂CH₂CH₃ group, —OCH₂CH₂CH₂CH₃ group, and

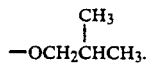

The reaction may be carried out at 20° to 100° C. for 1 to 5 hours.

The above-mentioned intramolecular and/or intermolecular condensation product can be produced by heating (usually 50° to 150° C.) under reduced pressure the organosilicon compound of formula (1) obtained by the first or second process for 1 to 5 hours.

The new organosilicon compound of the present invention has at least one β-diketone or β-ketoester structure and at least one hydrolyzable group in one molecule. Therefore, it finds use in a wide variety of application areas. Examples of the applications are provided below.

(1) Immobilized catalysts: Immobilized catalysts for various reactions can be produced by treating the surface of a carrier (such as glass beads, silica, ceramics, and ceramics moldings) with the organosilicon compound of the present invention, and then treating the carrier with a metal compound, thereby forming a metal chelate complex on the surface of the carrier.

(2) Adsorption and recovery of metal compounds: Metals can be adsorbed and recovered from a solution by dipping in the solution a carrier treated with the organosilicon compound in the same manner as above. The recovery may be accomplished continuously or batchwise. The carrier treated with the organosilicon compound is highly effective in recovery of useful metals and removal of harmful metals from waste water.

(3) Curing catalysts for organopolysiloxanes and epoxy resins: The organosilicon compound of the present invention reacts with a metal compound, thereby enhancing the mutual action between silicon and metal. Therefore, it increases the activity of the curing catalyst for organopolysiloxanes and epoxy resins. In addition, the organosilicon compound takes in a metal and stabilizes it. Therefore, it functions as an effective curing catalyst for organopolysiloxanes and epoxy resins.

(4) Adhesion promoters: The organosilicon compound is useful for improving the bond strength and water resistance of a resin bonded to a glass object. This is accomplished by treating a glass object with the organosilicon compound and then with a metal compound, and pouring an epoxy resin or the like onto (or into) the glass object. The treatment ensures the complete reaction at the interface between the glass object and the resin.

To further illustrate the invention, and not by way of limitation, the following examples and referential examples are given.

EXAMPLE 1

In a 1-liter separable flask equipped with a thermometer, nitrogen introducing pipe, Dimroth condenser, and stirrer were placed 184 g (1.0 mol) of allyl diacetoacetate, 300 g of toluene (as a solvent), and 10% chloroplatinic acid solution in toluene (containing 1.0 g or $5.0 \times 10^{-5}$ mol of platinum). To the flask was added dropwise at 40° C. under a nitrogen stream 122 g (1.0 mol) of trimethoxysilane. An exothermic reaction took place, indicating that the addition reaction was proceeding. After the dropwise addition of trimethoxysilane, stirring was continued for 3 hours. At the end of the reaction, a sample was taken from the reaction liquid, and an alkaline water was added to the sample to see the evolution of hydrogen gas. Evolution of hydrogen gas was not observed. This indicates that the trimethoxysilane was completely consumed at the end of the reaction.

The reaction liquid was freed of solvent under reduced pressure at room temperature. Thus there was obtained 304 g of reaction product-A. Reaction product-A was examined for infrared absorption spectrum. High peaks appeared at 1085 cm$^{-1}$ and 1715 cm$^{-1}$. These peaks are assigned to the alkyloxysilyl group and ketone or ester group, respectively. The peak at 990 cm$^{-1}$ assigned to the terminal vinyl in the raw material disappeared, which indicates the completion of the hydrosilylation reaction.

The reaction product-A was also examined for NMR spectrum. There was obtained a spectrum having the following chemical shift, the assignment of which is also shown below.

0.65 ppm (t, 2H): —CH$_2$—CH$_2$—C$\underline{H}_2$—Si≡

1.5–2.0 ppm (m, 2H): —CH$_2$—C$\underline{H}_2$—CH$_2$—Si≡

2.3 ppm (s, 6H): C$\underline{H}_3$—CO—

3.5 ppm (s, 9H): —Si(OC$\underline{H}_3$)$_3$ 3.7–4.1 ppm (m, 3H): —COO—C$\underline{H}_2$—, 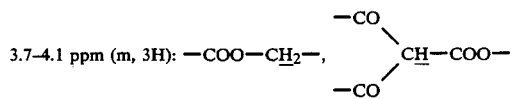

The reaction product-A was subjected to elemental analysis. The results are given below.

|   | Found | Calcd. |
|---|---|---|
| C | 47.8% | 47.04% |
| H | 7.0% | 7.24% |
| O | 35.9% | 36.55% |

According to the spectral criteria and elemental analysis, it was found that the reaction product-A is a hydrosilylated compound of the formula below.

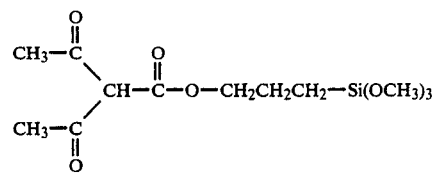

In the meantime, the signal (at 5.1–6.3 ppm) assigned to the terminal vinyl group in allyl diacetoacetate as the raw material completely disappeared in the reaction product-A.

EXAMPLE 2

The same procedure as in Example 1 was repeated except that allyl diacetoacetate was replaced by 142 g (1.0 mol) of allyl acetoacetate. There was obtained 260 g of reaction product-B.

Reaction product-B was examined for infrared absorption spectrum. High peaks appeared at 1085 cm$^{-1}$, 1715 cm$^{-1}$, and 1740 cm$^{-1}$. These peaks are assigned to the alkyloxysilyl group, ketone group, and ester group, respectively.

The reaction product-B was also examined for NMR spectrum. There was obtained a spectrum having the following chemical shift, the assignment of which is also shown below.

0.65 ppm (t, 2H): —CH$_2$—CH$_2$—C$\underline{H}_2$—Si≡

1.5–2.0 ppm (m, 2H): —CH$_2$—C$\underline{H}_2$—CH$_2$—Si≡

2.3 ppm (s, 3H): C$\underline{H}_3$—CO—

3.5 ppm (s, 9H): —Si(OC$\underline{H}_3$)$_3$ 3.6–3.7 ppm (m, 2H): —CO—C$\underline{H}_2$—COO—

4.0–4.2 ppm (m, 2H): —COO—C$\underline{H}_2$—

The reaction product-B was subjected to elemental analysis. The results are given below.

|   | Found | Calcd. |
|---|---|---|
| C | 46.0% | 45.44% |
| H | 7.4% | 7.63% |
| O | 35.8% | 36.31% |

According to the spectral criteria and elemental analysis, it was found that the reaction product-B is a hydrosilylated compound of the formula below.

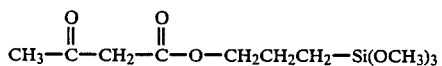

CH₃—C(=O)—CH₂—C(=O)—O—CH₂CH₂CH₂—Si(OCH₃)₃

EXAMPLE 3

Upon heat treatment under reduced pressure at 120° C. for 2 hours, 304 g of the reaction product-A obtained in Example 1 gave 242 g of reaction product-C. All of the volatile matter was methanol.

The reaction product-C was also examined for NMR spectrum. A peak assigned to an olefinic protone appeared at 4.6–5.6 ppm. The singlet peak at 3.5 ppm assigned to the —OCH₃ group became small.

According to the spectral criteria, it was found that the reaction product-C was formed from the reaction product-A through the intramolecular or intermolecular enolization that brings about condensation with the elimination of methanol.

EXAMPLE 4

In a 1-liter separable flask equipped with a thermometer, nitrogen introducing pipe, Dimroth condenser, and stirrer were placed 130 g (1.0 mol) of ethyl acetate and 200 g of toluene (as a solvent). To the flask was added dropwise at room temperature under a nitrogen stream 193 g (1.0 mol) of 28% methanol solution of sodium methylate. After the dropwise addition, the reactants were heated with stirring for 3 hours under the refluxing of methanol. To the reactants was added dropwise 199 g (1.0 mol) of γ-chloropropyltrimethoxysilane. After the dropwise addition, the reactants were heated with stirring for 3 hours under the refluxing of methanol. At the end of the reaction, a sample was taken from the reaction liquid, and it was examined by gas chromatography to confirm that the raw material was completely consumed.

The reaction liquid was freed of solvent by distillation and also freed of salt. Thus there was obtained 275 g of reaction product-D. Reacton product-D was examined for infrared absorption spectrum. High peaks appeared at 1085 cm⁻¹, 1715 cm⁻¹, and 1740 cm⁻¹. These peaks are assigned to the alkyloxysilyl group, ketone group, and ester group, respectively.

The reaction product-D was also examined for NMR spectrum. There was obtained a spectrum having the following chemical shift, the assignment of which is also shown below.

0.65 ppm (t, 2H): —CH₂—CH₂—CH₂—Si≡

1.0 ppm (t, 3H): —COO—CH₂—CH₃

1.5–2.0 ppm (m, 4H): —CH₂—CH₂—CH₂—Si≡

2.3 ppm (s, 3H): CH₃—CO—

3.5 ppm (s, 9H): —Si(OCH₃)₃

3.8–3.9 ppm (m, 1H): CH₃—CO—CH—COO—

4.1 ppm (q, 2H): —COO—CH₂—CH₃

The reaction product-D was subjected to elemental analysis. The results are given below.

|   | Found | Calcd. |
|---|---|---|
| C | 50.6% | 49.29% |
| H | 7.7% | 8.27% |
| O | 31.8% | 32.83% |

According to the spectral criteria and elemental analysis, it was found that the reaction product-D is an organosilicon compound of the formula below.

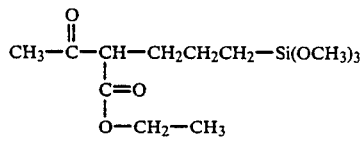

EXAMPLE 5

The same procedure as in Example 4 was repeated except that ethyl acetate was replaced by 100 g (1.0 mol) of acetyl acetone. There was obtained reaction product-E.

Reaction product-E was examined for infrared absorption spectrum. High peaks appeared at 1085 cm⁻¹ and 1715 cm⁻¹. These peaks are assigned to the alkyloxysilyl group and ketone group, respectively.

The reaction product-E was also examined for NMR spectrum. There was obtained a spectrum having the following chemical shift, the assignment of which is also shown below.

0.65 ppm (t, 2H): —CH₂—CH₂—CH₂—Si≡

1.5–2.0 ppm (m, 4H): —CH₂—CH₂—CH₂—Si≡

2.35 ppm (s, 6H): CH₃—CO—CH—CO—CH₃

3.5 ppm (s, 9H): —Si(OCH₃)₃

3.8–3.9 ppm (m, 1H): CH₃—CO—CH—CO—CH₃

The reaction product-E was subjected to elemental analysis. The results are given below.

|   | Found | Calcd. |
|---|---|---|
| C | 51.6% | 50.36% |
| H | 8.1% | 8.45% |

| | Found | Calcd. |
|---|---|---|
| O | 29.0% | 30.49% |

According to the spectral criteria and elemental analysis, it was found that the reaction product-E is an organosilicon compound of the formula below.

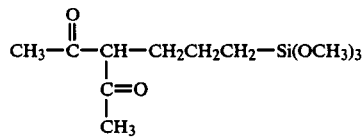

REFERENTIAL EXAMPLE 1

A 1% solution of reaction product-A was prepared by dissolving reaction product-A in a water/methanol mixture (10/90 by weight) containing 1% by weight of acetic acid, with continuous thorough stirring for 30 minutes. In the solution was dipped instantaneously a glass cloth which had previously undergone heat cleaning. The glass cloth was air-dried and then cured at 100° C. for 15 minutes. Thus there was obtained a colorless treated glass cloth.

The treated glass cloth was dipped in a 1% aqueous solution (colorless and clear) of aluminum sulfate. Upon air-drying, the glass cloth turned yellow. This indicates that aluminum was adsorbed and immobilized in the form of chelate complex on the glass cloth. According to emission spectrochemical analysis, the colored glass cloth was found to contain 0.05% by weight of aluminum.

The glass cloth on which aluminum was immobilized was dipped in an epoxy resin composition. The glass cloth was dried at 160° C. for 6 minutes and then at 140° C. for 4 minutes to make a prepreg for epoxy laminated sheet. The resin content of the prepreg was 50%.

| Epoxy resin composition | |
|---|---|
| Bisphenol type epoxy (Epikote ® 1001*) | 80 parts by weight |
| Cresol-novolac type epoxy resin (Epikote ® 154*) | 20 parts by weight |
| Dicyandiamide | 4 parts by weight |
| Benzyldimethylamine | 0.2 parts by weight |
| Methyl ethyl ketone | 20 parts by weight |
| Methyl cellosolve | 45 parts by weight |

*manufactured by Yuka Shell Epoxy Co., Ltd.

Eight pieces of the thus prepared prepreg were laminated one over another, with the top and bottom clad with copper foil. The laminate was heated at 170° C. for 3 minutes under contact pressure and then pressed under 35 kg/cm2 for 40 minutes, followed by post curing at 180° C. for 1 hour. Thus there was obtained an epoxy laminated sheet (I).

The same procedure as above was repeated except that the reaction product-A was replaced by γ-glycidoxy-propyltrimethoxysilane (KBM-403). There was obtained an epoxy laminated sheet (II).

The epoxy laminated sheets (I) and (II) obtained as mentioned above were dipped in a solder bath at 260° C. for 30 seconds. The surface of the sheets was examined for damage. Results are shown below.

| Organosilicon compound | Damaged area (%) |
|---|---|
| Epoxy laminated sheet (I) (Reaction product-A) | 5.2 |
| Epoxy laminated sheet (II) (KBM-403) | 21.6 |

It is noted that the best result is obtained with a glass cloth treated with the reaction product-A and aluminum. It is thought that aluminum permits the epoxy resin to come into close contact with the interface, thereby increasing the bond strength and improving water resistance.

REFERENTIAL EXAMPLE 2

To 306 g of the reaction product-A was added 510 g of isopropyl alcohol, and the resulting mixture was further mixed with 204 g of triisopropoxy aluminum at room temperature. The mixture turned reddish brown, with slight heat generation. The thus obtained mixture was designated as catalyst-F.

In a 1-liter separable flask were placed 125 g of γ-glycidoxypropylmethyldiethoxysilane (KBE-402) 100 g of γ-glycidoxypropyltrimethoxysilane (KBM-403), and 80 g of isobutyl alcohol. The reactants were stirred with ice cooling. To the flask was added dropwise 38 g of 0.05N hydrochloric acid over 60 minutes. To the flask was further added 300 g of methanol silica sol (made by Nissan Chemical Industries, Ltd.). The reaction mixture was aged at 20°–25° C. for 16 hours. To the reaction mixture were added 0.4 g of polyether silicone (KP-341), 50 g of ethanol, 70 g of ethyl cellosolve, and 3.0 g of catalyst-F, followed by stirring for 30 minutes. Thus there was obtained coating solution-G.

An alkali-treated plastic lens (made of allyl biscarbonate resin (CR-39 ®)) was dipped in the coating solution-G and then raised out of the solution at a rate of 20 cm/min. After air-drying, the coating was cured at 120° C. for 2 hours. Thus there was obtained a coated plastic lens (I). For comparison, the same procedure as above was repeated except that the catalyst-F was replaced by triacetylacetone aluminum (Al(acac)$_3$). Thus there was obtained a coated plastic lens (II).

The coated plastic lenses (I) and (II) were examined for wear resistance in the following manner. The lens sample was rubbed with #0000 steel wool moving back and forth 100 cycles under a load of 500 g. The surface of the lens was examined for scratches and haze.

The coated plastic lenses (I) and (II) were dyed by dipping in a 1% aqueous solution of disperse dye brown-D (made by Seiko Co., Ltd.) at 87° C. for 5 minutes. The dyed plastic lenses were examined for light transmittance. The results are given below.

| | Surface state | Light transmittance (%) |
|---|---|---|
| Plastic lens (I) (Catalyst-F) | Very few scratches | 71.6 |
| Plastic lens (II) (Al(acac)$_3$) | Deep scratches | 62.4 |

It is noted from the above results that the catalyst-F has a high catalytic activity and hence provides a hard coating film having high scratch resistance. Moreover, the catalyst-F cures the coating film to such an extent that the coating film is dyed very little. This is indicated by the high light transmittance.

What is claimed is:

1. An organosilicon compound represented by formula (1) below:

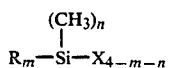

wherein R denotes a monovalent organic group containing one or more β-diketone or β-ketoester structures having 4 to 20 carbon atoms, said monovalent organic group being selected from the group consisting of

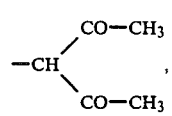

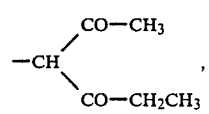

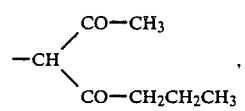

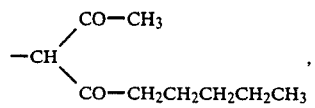

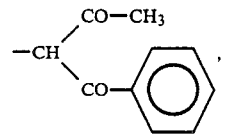

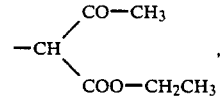

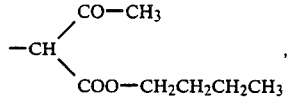

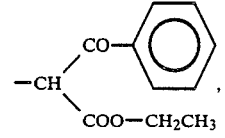

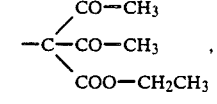

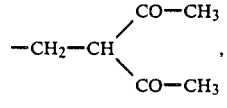

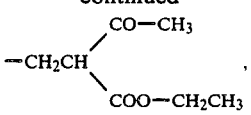

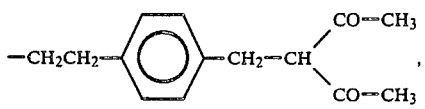

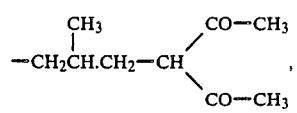

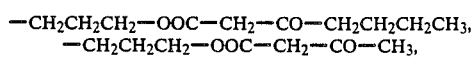

—CH₂CH₂CH₂—OOC—CH₂—CO—CH₂CH₂CH₂CH₃,
—CH₂CH₂CH₂—OOC—CH₂—CO—CH₃,

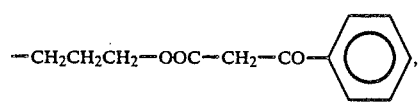

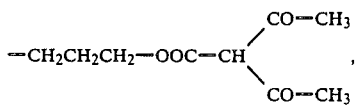

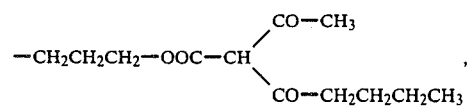

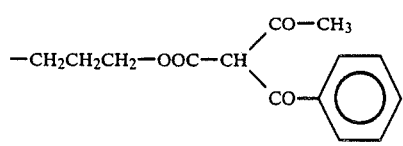

and

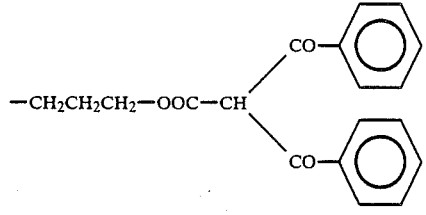

wherein X denotes a hydrolyzable group selected from the group consisting of —Cl, —Br, —I, —OCH, —OCH₃CH₂CH₃, —OCH₂CH₂CH₃,

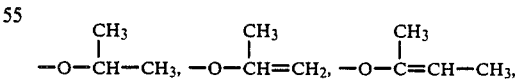

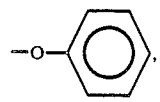

—OOC—CH₃, —OOC—CH₂CH₂CH₃, NH₂, —NH—CH₃ and —NH—CH₂CH₂CH₂CH₃; m denotes 1, 2 or 3; n denotes 0, 1 or 2; and $1 \leq m + n \leq 3$.

2. An organosilicon compound selected from the group consisting of

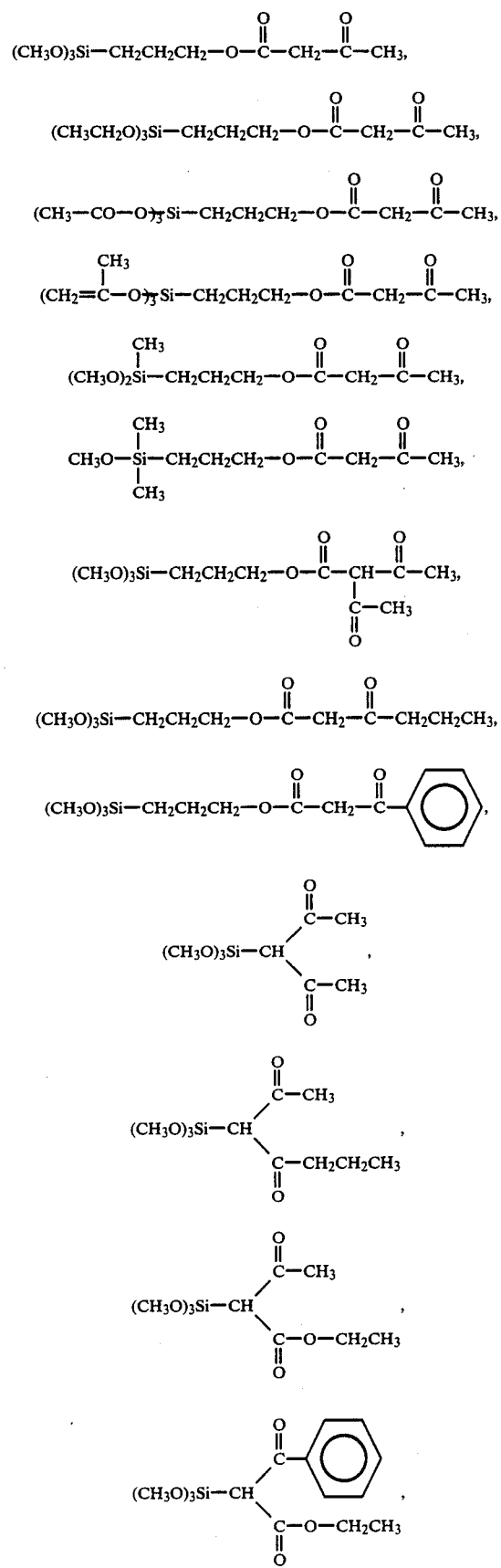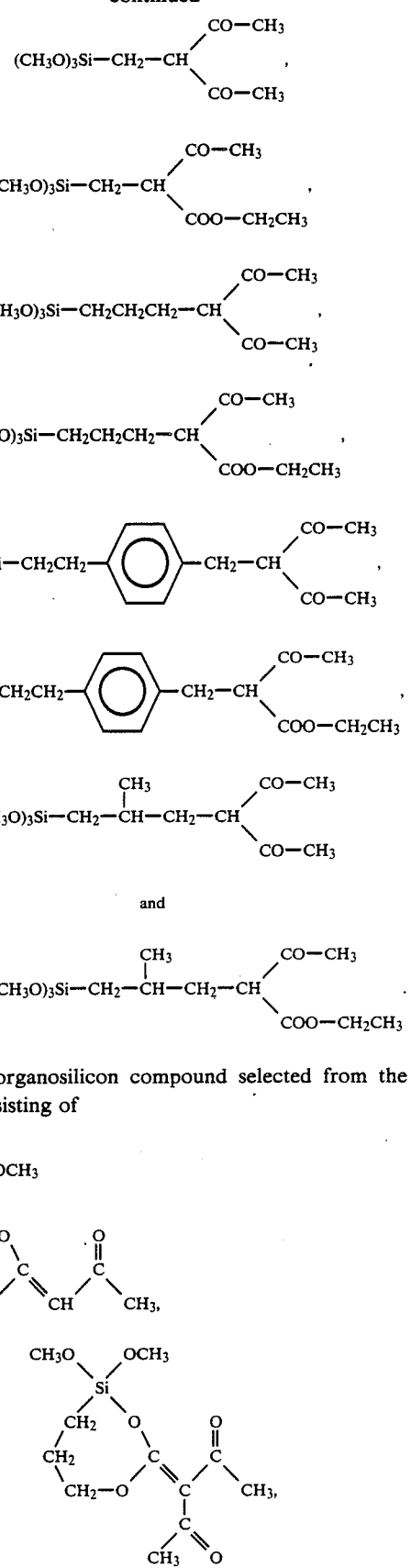
3. The organosilicon compound selected from the group consisting of
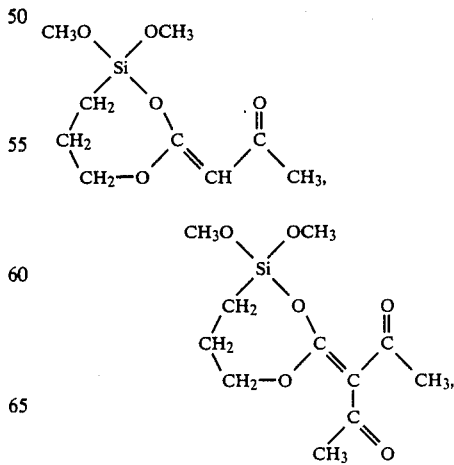

-continued

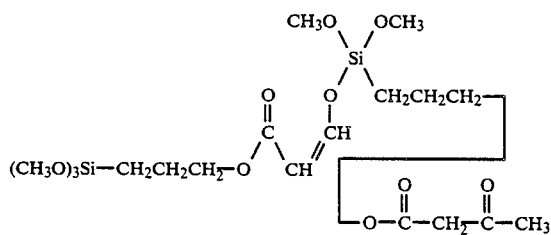

and

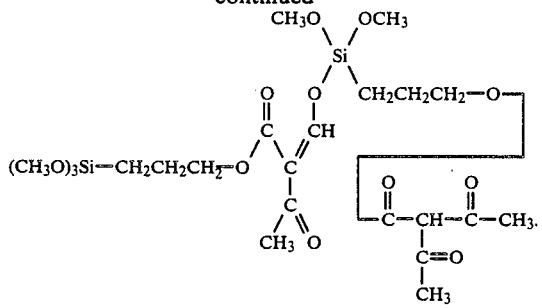

4. An organosilicon compound produced through an intermolecular of intramolecular condensation between an OH group and hydrolyzable group, the OH group being the one formed through the keto/enol tautomerism of a β-diketone or β-ketoester contained in the organosilicon compound represented by formula (1) according to claim 1, and the hydrolyzable group being the one contained in the organosilicon compound represented by formula according to claim 1.

* * * * *